US006537290B2

(12) United States Patent
Adams et al.

(10) Patent No.: US 6,537,290 B2
(45) Date of Patent: Mar. 25, 2003

(54) SEALING ACCESS CANNULA SYSTEM (75) Inventors: Leland R. Adams, Ansonia, CT (US); Scott Reed, Monroe, CT (US); Alan B. Bachman, New Haven, CT (US); William J. Allen, Stratford, CT (US); Robert Chapolini, Phoenix, AZ (US)

(73) Assignee: Edwards Lifesciences Corporation, Irvine, CA (US)

( * ) Notice: Subject to any disclaimer, the term of this patent is extended or adjusted under 35 U.S.C. 154(b) by 47 days.

(21) Appl. No.: 09/800,390

(22) Filed: Mar. 5, 2001

(65) Prior Publication Data

US 2002/0128602 A1 Sep. 12, 2002

(51) Int. Cl.⁷ .................. A61B 17/32; A61B 17/34; A61M 25/00; A61M 5/00
(52) U.S. Cl. .................. 606/167; 606/185; 604/264
(58) Field of Search .................. 606/213, 167, 606/185

(56) References Cited

U.S. PATENT DOCUMENTS

| | | | |
|---|---|---|---|
| 2,835,253 A | | 5/1958 | Borgeson |
| 5,725,544 A | | 3/1998 | Rygaard |
| 5,727,569 A | | 3/1998 | Benetti et al. |
| 5,743,881 A | * | 4/1998 | Demco ............ 604/158 |
| 5,829,447 A | | 11/1998 | Stevens et al. |
| 5,855,614 A | | 1/1999 | Stevens et al. |
| 5,875,782 A | | 3/1999 | Ferrari et al. |
| 5,882,331 A | * | 3/1999 | Sasaki ............ 128/898 |
| 5,924,424 A | | 7/1999 | Stevens et al. |
| 5,972,020 A | | 10/1999 | Carpentier et al. |
| 5,980,455 A | | 11/1999 | Daniel et al. |
| 5,984,941 A | * | 11/1999 | Wilson et al. ...... 604/256 |
| 6,007,523 A | | 12/1999 | Mangosong |
| 6,017,304 A | | 1/2000 | Vierra et al. |
| 6,032,672 A | | 3/2000 | Taylor |
| 6,033,420 A | | 3/2000 | Hahnen |
| 6,063,099 A | * | 5/2000 | Danks et al. ...... 604/264 |
| 6,079,414 A | | 6/2000 | Roth |
| 6,099,498 A | | 8/2000 | Addis |
| 6,110,187 A | | 8/2000 | Donlon |
| 6,162,209 A | * | 12/2000 | Gobron et al. ...... 606/1 |
| 6,165,183 A | | 12/2000 | Kuehn et al. |
| 6,258,069 B1 | | 7/2001 | Carpentier et al. |
| 6,269,819 B1 | | 8/2001 | Oz et al. |

FOREIGN PATENT DOCUMENTS

| | | |
|---|---|---|
| EP | 0745350 | 12/1996 |
| EP | 0791329 | 8/1997 |
| EP | 0791330 | 8/1997 |
| WO | WO96/32882 | 10/1996 |
| WO | WO98/24372 | 6/1998 |
| WO | WO00/54678 | 9/2000 |
| WO | WO00/59382 | 10/2000 |
| WO | WO00/60995 | 10/2000 |
| WO | WO00/74574 | 12/2000 |
| WO | WO01/26557 | 4/2001 |

* cited by examiner

Primary Examiner—Henry C. Yuen
Assistant Examiner—John Fristor
(74) Attorney, Agent, or Firm—Debra D. Condino; John Christopher James

(57) ABSTRACT

The present invention discloses a system and method for providing sealable access to a viscus region or hollow organ and performing surgical procedures therein. The present invention is particularly useful in providing access to a patients heart without arresting the heart. The access system comprises a tissue stabilizer to provide a stable work area in a dynamic environment. A puncture device is inserted into the tissue stabilizer, which forms a puncture hole within the heart tissue. Thereafter, a sealing device, for example a sealing balloon, is inserted through the puncture hole and engages the interior tissue. A sealing cannula may then be advanced into and sealably engages the tissue.

21 Claims, 14 Drawing Sheets

SEALING ACCESS CANNULA SYSTEM

BACKGROUND OF THE INVENTION

Presently, a variety of surgical procedures require the insertion of surgical devices into an arterial or venous vessel, a viscus region, or alternatively, into the heart of a patient. These procedures include diagnostic procedures, radiological procedures, coronary and peripheral angioplasties, thorascopic, laparoscopic, or endoscopic surgeries. Generally, these procedures require accessing the area of interest, forming an incision through the exterior wall of a body vessel or organ, and inserting an implement, commonly a trocar or other catheter-like surgical device, through the opening. Considerable care must be exercised during the insertion process to avoid introducing air into the viscus region, blood vessel, or heart. Furthermore, the quantity of blood loss through the incision should be limited.

Commonly, cannula devices are used to avoid the risk of air embolism and limit blood loss through the incision, while providing access into the blood vessel or organ. Typically, an incision closing device, for example a purse string suture, is applied to the tissue surrounding the incision. Thereafter, the cannula is inserted into the incision and the incision closing device is used to sealably engage the cannula. The above disclosed insertion method may result in the unwanted application of pressure to the incision area and could result in damage to the tissue located within the blood vessel or body organ.

Current cannula devices encounter additional problems in surgeries involving a beating heart. For example, there is an increased risk of damage to the beating heart during the insertion of the cannula. Generally, the heart is comprised of four chambers separated by artrio-ventricular valves. The insertion process disclosed above may result in compressive force being applied to the heart, thereby causing a disruption in normal circulatory function. Of equal concern is an increased risk of damaging the internal tissues and valves of the beating heart. Additionally, the internal pressure exerted during a cardiac cycle commonly results in chronic seepage or leakage at the incision-cannula interface. While excessive bleeding is common with a person having a normal blood-clotting response, this problem is magnified in persons utilizing anticoagulation medication. These medications are commonly prescribed to persons suffering from some forms of heart disease, for example, hypertension. As such, an interventional surgical procedure may be required should these medications fails to adequately address the patient's heart condition.

Thus, there is a need for a cannula system for use on viscus regions and hollow organs of a body. Furthermore, the system would be capable of attaching to a beating heart or other vessel or organ and provide a stable working environment on a dynamic organ, while reducing the blood loss through and around the cannula.

BRIEF SUMMARY OF THE INVENTION

The present invention solves the problem of gaining access to a viscus region or hollow organ of a patient while limiting excess blood loss through the access incision. Additionally, the present invention reduces or eliminates the likelihood of damage to the internal components of the organ during cannula insertion. The present invention is particularly well suited for procedures involving the heart. More particularly, the present invention permits access to the internal region of the heart without requiring the heart to be arrested. Additionally, the present invention permits remote cannulization of a hollow organ or viscus region.

In one aspect, the present invention provides an access system comprising a tissue stabilizer capable of attachment to the viscus region or hollow organ, and a sealing cannula. A puncture device is inserted into the tissue stabilizer and forms a puncture hole in the tissue. Thereafter a sealing device is inserted into the tissue stabilizer and sealably engages the tissue around the puncture hole. A cutting trocar may then introduced into the puncture hole to enlarge the orifice to receive the sealing cannula. A sealing cannula is inserted into the orifice and a purse string suture is applied, thereby sealing the cannula/tissue interface.

In another aspect of the present invention, a tissue stabilizer is disclosed herein. The tissue stabilizer comprises a central lumen in communication with a receiving flange and an attachment flange having a vacuum port positioned thereon. The vacuum port is in communication with a vacuum chamber located within the attachment flange. In an alternate embodiment a purse string template is positioned on the attachment flange.

In yet another embodiment, the present invention discloses a sealing cannula having a device body in communication with a device lumen. The device body comprises a sealing washer and a guide member positioned within a receiving lumen, and a sealing member in communication with said receiving lumen and the device lumen.

The present invention also discloses a method of providing access to a viscus region or hollow organ. Other objects and further features of the present invention will become apparent from the following description when read in conjunction with the attached drawings.

DESCRIPTION OF THE PREFERRED EMBODIMENT

Disclosed herein is a description of various illustrated embodiments of the invention. This description is not to be taken in a limiting sense, but is made merely for the purpose of illustrating the general principles of the invention. The section titles and overall organization of the present description are for the purpose of convenience only and are not intended to limit the present invention.

The viscus access system of the present invention is generally used in surgical procedures to permit the introduction of surgical devices or implements while limiting patient blood loss. More specifically, the present invention is used to form an access point within a hollow organ or viscus body. For example, the present invention is particularly useful in providing sealed access to a heart without requiring the heart to be arrested. As those skilled in the art will appreciate, the present invention may be utilized as a system or, in the alternative, individual elements of the system may be utilized separately as desired. It is anticipated as being within the scope of the present invention to produce an access system capable of functionally attaching to a plurality of organs within a body.

Figure 1A:
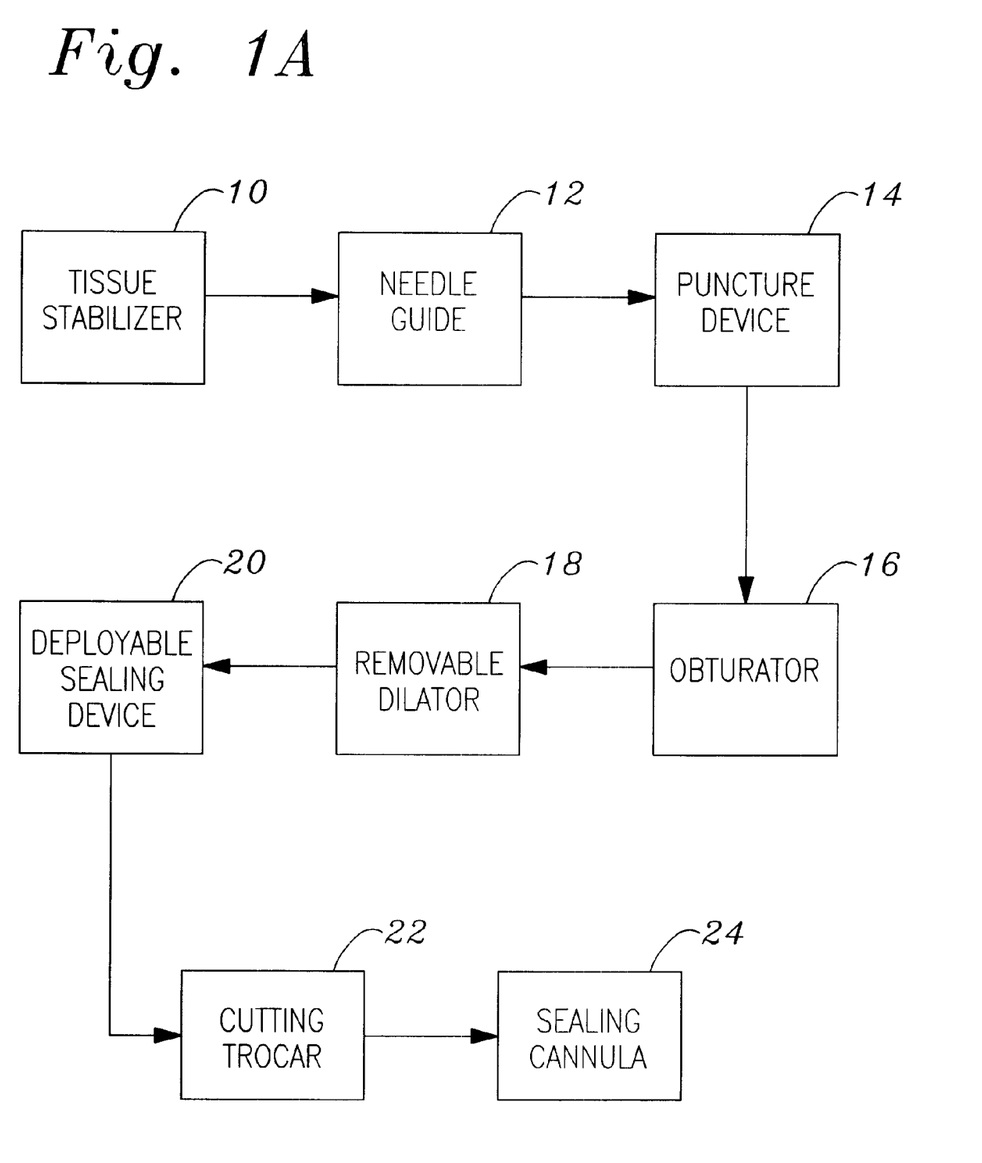
FIG. 1a is an operational flowchart of the various components of the sealing viscus access system.
Figure 1B:
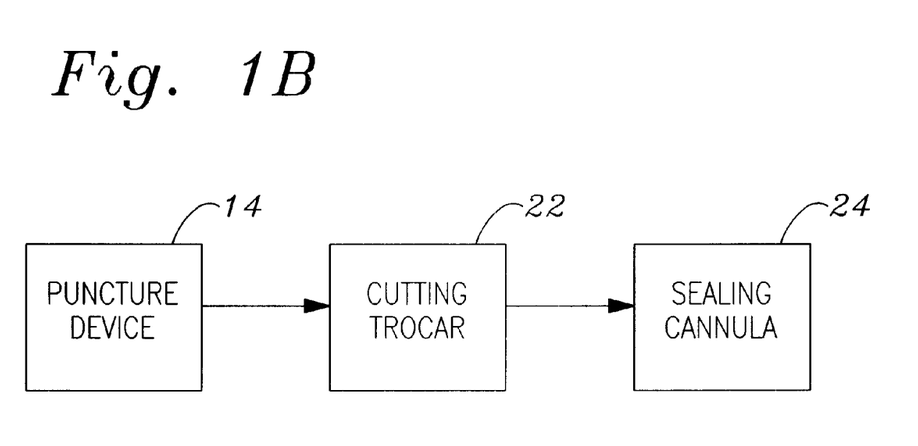
FIG. 1b is an alternate operational flowchart of various components of the sealing viscus access system.

FIG. 1a shows an operational use flow chart of the viscus access system having a tissue stabilizer 10, a needle guide 12, a puncture device 14, an obturator 16, a removable dilator 18, a deployable sealing device 20, a cutting trocar 22, and a sealing cannula 24. For clarity the individual elements of the present invention will be presented individually. It should be understood the present invention may be utilized in various procedures to sealably access hollow organs within a body, and to provide a device for introducing various surgical implements therein. As such, the flow chart presented in FIG. 1a provides one embodiment of use, and is not intended to be limiting. For example, an alternate operational use flow chart is presented in FIG. 1b. As shown in FIG. 1b, the system may comprise a puncture device 14, a cutting trocar 22, and a sealing cannula 24

Figure 2A:
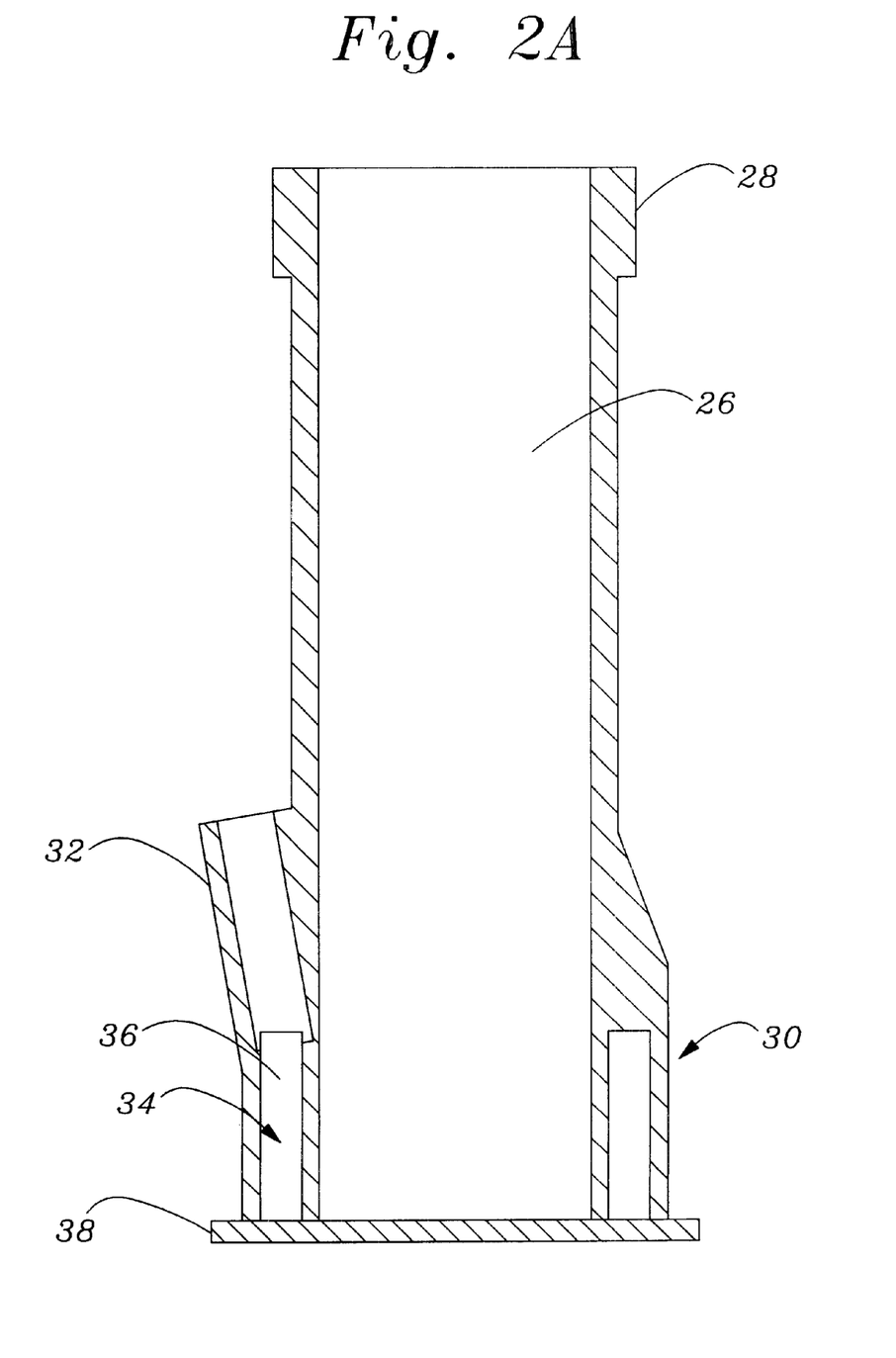
FIG. 2a is a cross sectional view of an embodiment of the tissue stabilizer of the present invention.
Figure 2B:
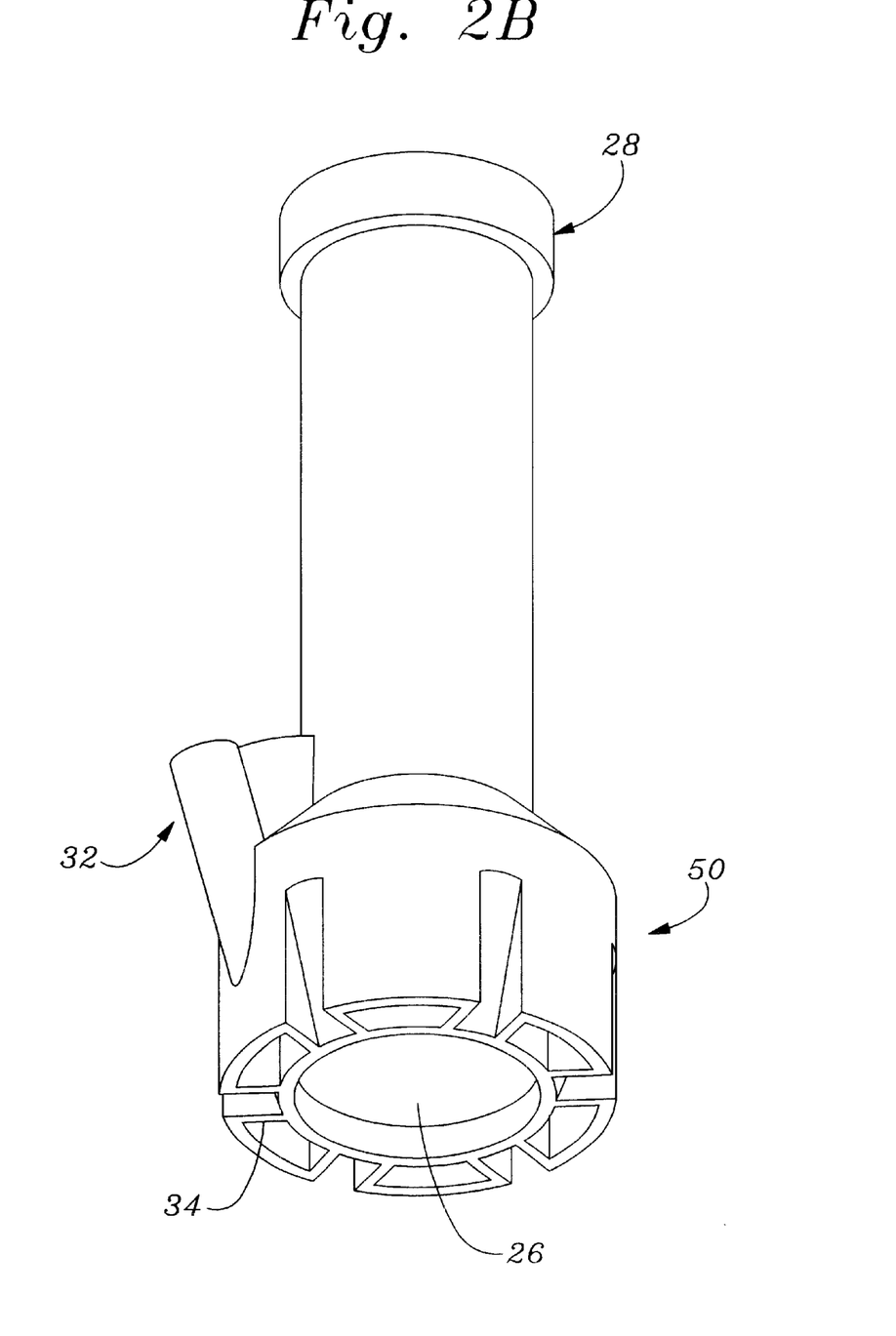
FIG. 2b is a perspective view of an embodiment of the tissue stabilizer of the present invention.

FIGS. 2a and 2b show the tissue stabilizer 10 of the present invention having a central lumen 26 positioned between a receiving flange 28 and an attachment flange 30. A vacuum port 32 is positioned on the attachment flange 30 and is in communication with a vacuum chamber 34 located within the attachment flange 30. As shown in FIG. 2a, the present embodiment may further comprise vanes 36 located within the vacuum chamber 34 to prevent tissue from collapsing into the vacuum port 32. The tissue stabilizer 10 may include a purse string template 38 located radially about the attachment flange 30, thereby aiding the surgeon in applying a purse string suture or other wound closing mechanism to the area. FIG. 2b shows a perspective view of the tissue stabilizer 10 without having a purse string template 38 disposed thereon. As those skilled in the art will appreciate, the present invention may be manufactured from a plurality of materials including, without limitation, biologically compatible metal, plastics, or elastomers.

Figure 3:
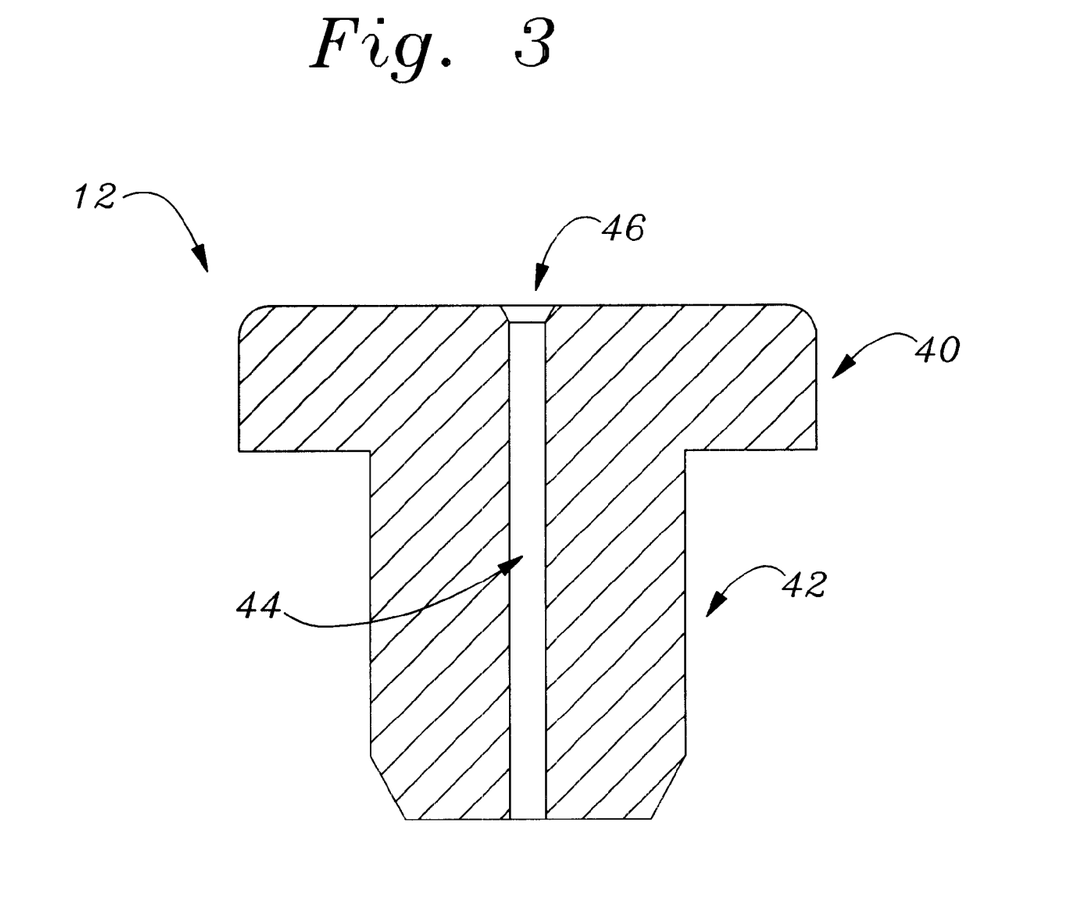
FIG. 3 is cross sectional view of the needle guide of the present invention.

FIG. 3 shows the needle guide 12 of the present invention having an insertion stop 40 attached to a guide body 42 defining a guide lumen 44 terminating in a receiving aperture 46 formed on the insertion stop 40. The needle guide 12 may be inserted into and sealably engage the receiving flange 28 of the tissue stabilizer 10. Those skilled in the art will appreciate the needle guide 12 may be manufactured from a plurality of materials including, for example, biologically compatible elastomers or polymers.

Figure 4:
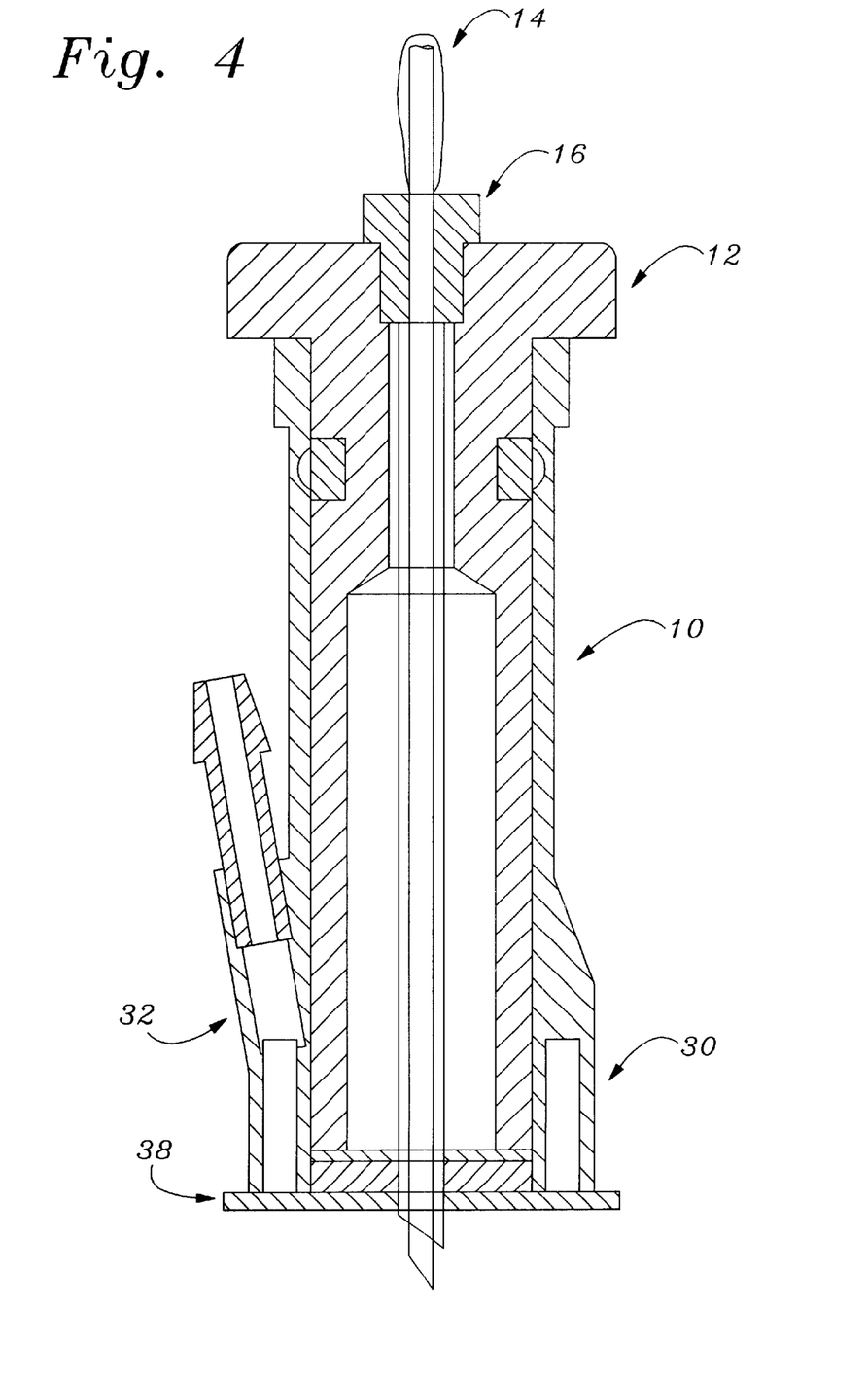
FIG. 4 is a cross sectional view of the tissue stabilizer of the present invention having a puncture device and a obturator positioned therein.

FIG. 4 shows the puncture device 14 located within an obturator 16 sealably engaging the needle guide 12 positioned within the tissue stabilizer 10. The puncture device 14 and obturator 16 puncture the tissue and enlarge the puncture site to permit the introduction of other devices. The puncture device 14 may comprise a plurality of tissue puncturing devices including, for example, a needle or a guidewire. The obturator 16 may be utilized to enlarge the puncture site formed in the tissue by the puncture device 14. The obturator 16 may be manufactured from a plurality of materials, including, for example, biologically compatible metals, plastic or elastomers. In an alternate embodiment, the puncture site is created and enlarged with a single device, for example, a large bore needle.

Figure 5:
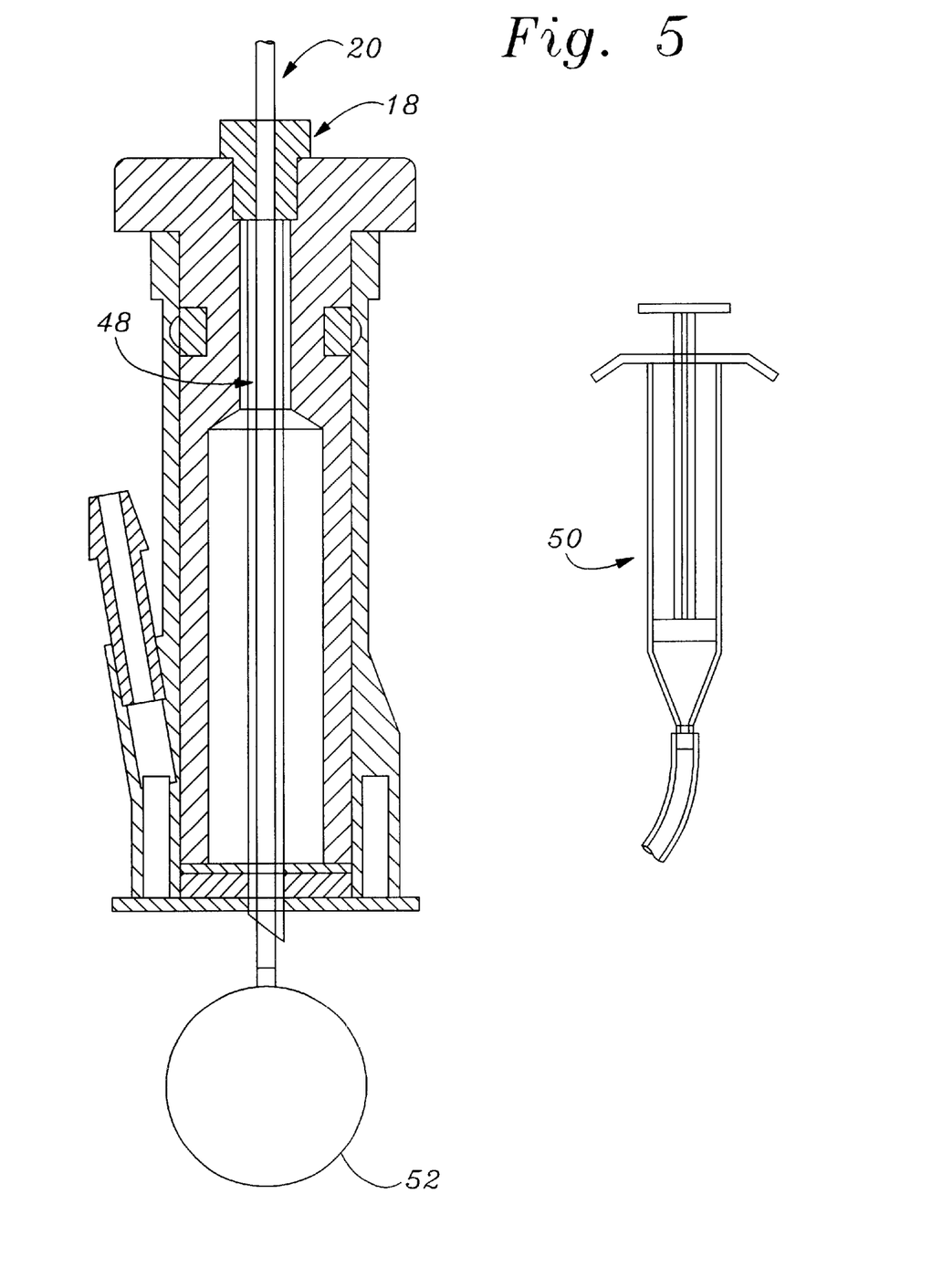
FIG. 5 is a cross sectional view of the tissue stabilizer or the present invention having a removable dilator and a sealing device positioned therein.

FIG. 5 shows a removable dilator 18 and sealing device 20 positioned within the central lumen 26 of the tissue stabilizer 10. The removable dilator 18 may comprise a plurality of devices including, for example, a peel-away dilator. The sealing device 20 comprises a transfer lumen 48 proximally terminating in an inflation device 50 and distally terminating in a sealing balloon 52. A plurality of inflation devices may be utilized to inflate the sealing balloon 52, including, for example, a syringe containing a biologically inert fluid such as saline.

Figure 6:
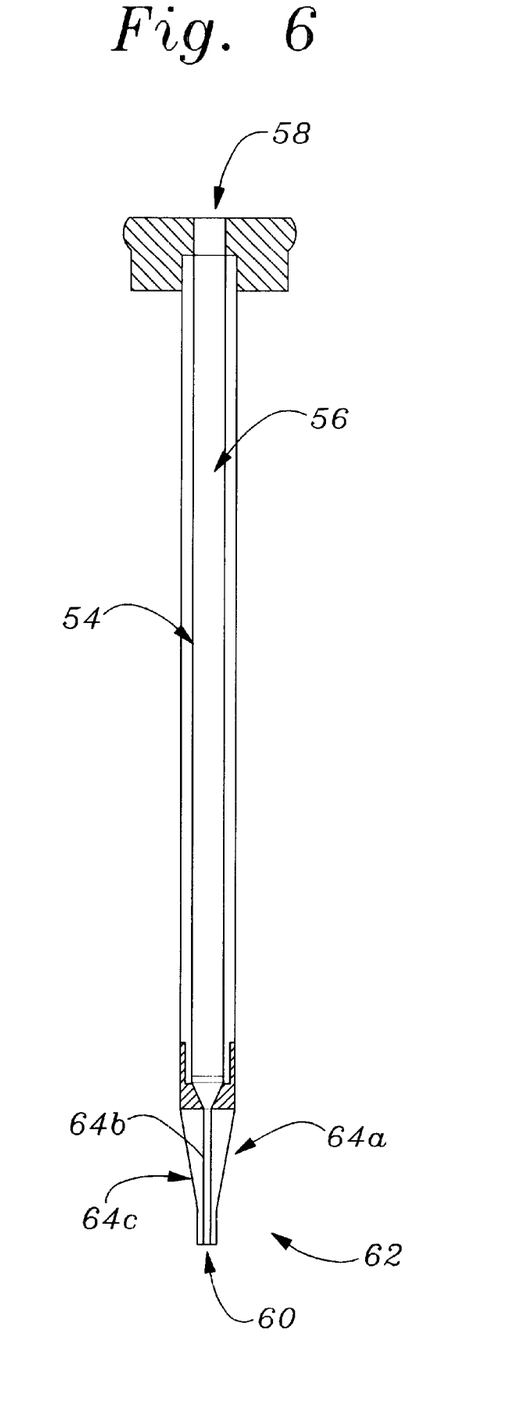
FIG. 6 is a cross sectional view of the cutting trocar or the present invention.

FIG. 6 shows the cutting trocar 22 of the present invention having an elongated body 54 defining a device lumen 56 therein. The proximal portion of the device lumen 56 terminates in a insertion inlet 58 and the distal portion terminated in insertion outlet 60. The distal portion of the cutting trocar 22 comprises a tissue cutting head 62. At least one cutting member is positioned- on the cutting head 62. As shown in FIG. 6, the cutting head 62 of the present embodiment comprises three cutting members 64a, 64b, and 64c, positioned radially thereon. The cutting trocar 22 of the present invention may be manufactured from a plurality of materials, including, for example, biologically compatible metals, plastics, or elastomers. In addition, the cutting trocar 22 of the present invention may be manufactured in a plurality of sizes to accommodate various hollow organs and viscus members of the body.

Figure 7:
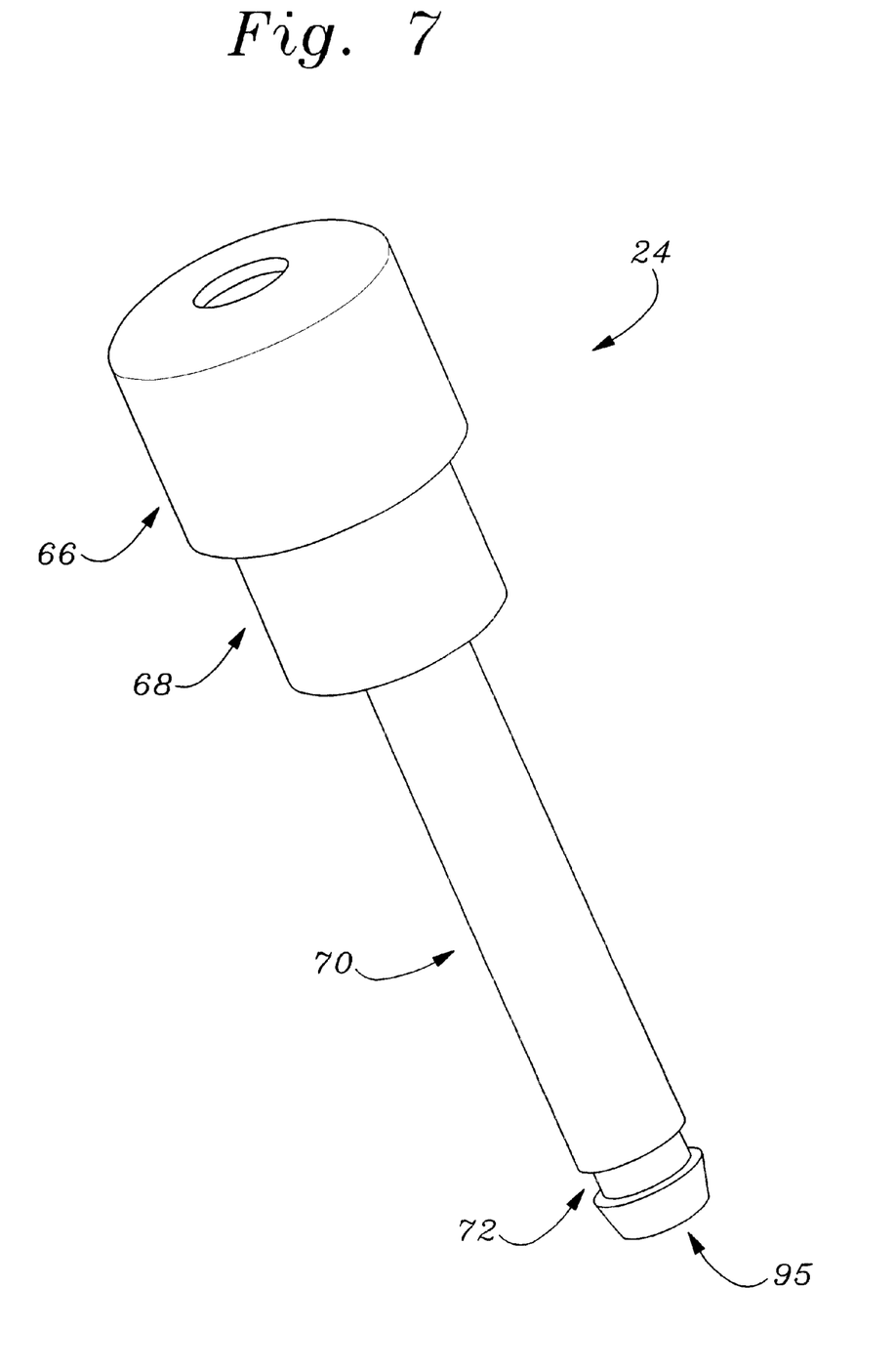
FIG. 7 is a perspective view of the sealing cannula of the present invention.

FIG. 7 shows the exterior sealing cannula of the present invention. As shown in FIG. 7, the sealing cannula 24 comprises an upper cannula body 66 attached to a lower cannula body 68 having a device channel 70 connected thereto. A tissue-engaging channel 72 is located near the distal portion of the device channel 70. The present invention may be manufactured from a plurality of materials or combinations of materials, including, elastomer, silicon, reinforced plastic, various plastic resins, and various metals. For example, the sealing components of the device may be manufactured from a flexible elastomer while the exterior structures may be manufactured from reinforced plastics.

Figure 8A:
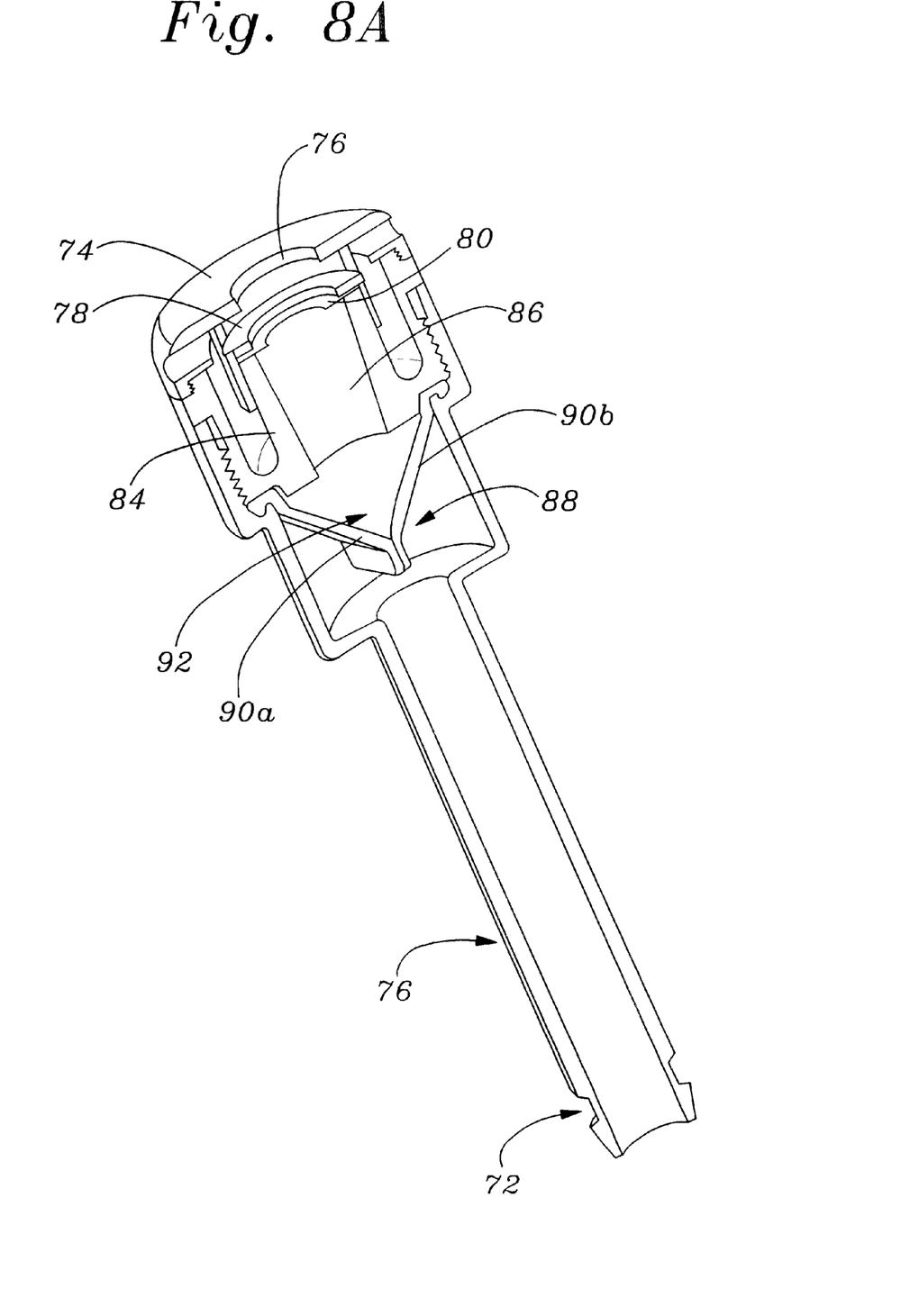
FIG. 8a is a cross sectional view of the sealing cannula of the present invention.
Figure 8B:
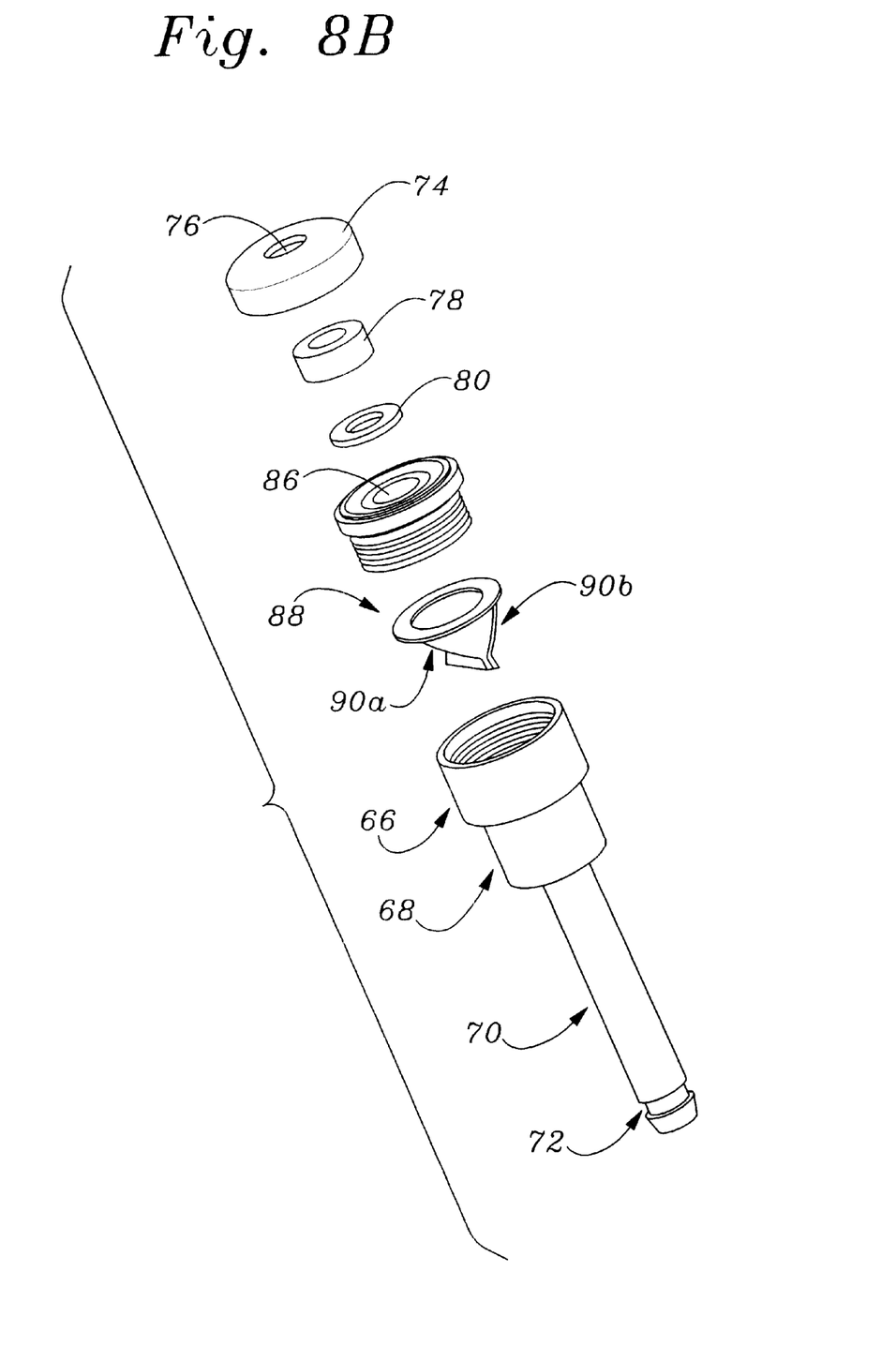
FIG. 8b is an exploded view of the sealing cannula of the present invention.

FIGS. 8a and 8b show the internal components of the sealing cannula 24. As shown in FIG. 8a, the sealing cannula 24 comprises a cannula cap 74 having an access orifice 76 formed thereon positioned on the upper cannula body 66. The cannula cap 74 may be attachable to the upper cannula body 66 in a variety of ways, including for example, in snap fit, screw relation, or adhesively joined. An o-ring 78 and sealing washer 80 defining a washer orifice 82 are positioned proximal the cannula cap 74, and act as a sealing conduit between the cannula cap 74 and the guide member lumen 86 formed in the guide member 84. The guide member 84 is attached to the upper cannula body 66 in screw-like fashion. In alternative embodiments, the guide member 84 may be attached to the upper cannula body 66 in slip-fit relation, snap-fit relation, or other manners known in the art. As shown in FIG. 8, the guide member lumen 86 is tapered. In another embodiment the walls of the guide member 84 forming the guide member lumen 86 maybe substantially parallel. FIG. 8b shows an exploded view of the sealing cannula 24.

The present invention further comprises a sealing member 88 located within the lower cannula body 68 and in communication with the guide member lumen 86 and the device channel 94. The sealing member 88 prevents a backflow of blood or other material from entering the cannula. As shown, the sealing member 88 comprises a duckbill seal 90 having at least two sealing leafs 90a and 90b forming a sealing receiver 92. In alternative embodiments, various sealing devices may be incorporated into the sealing cannula 24, including, for example, sealing irises and flapper valve devices.

Those skilled in the art will appreciate the degree of adaptability and servicability of the present invention. For example, the sealing cannula 24 may be easily adapted to sealably engage devices having various diameters. To adapt or service the device 24 the operator may remove one or all of following: the cannula cap 74, the o-ring 78, the sealing washer 80, the guide member 84, and the sealing member 88. The operator may then install new components having a larger or small internal apertures and reassemble the device. For example, the operator may replace a sealing washer 80 with another sealing washer 80 having a smaller washer orifice 82.

The present invention also teaches a method of using the sealing viscus access system to provide sealed access to a viscus body or hollow organ during a surgical procedure. FIGS. 9a–9K show one method of using the present invention to gain access to a viscus body, and should not be construed as limiting.

Figure 9A:
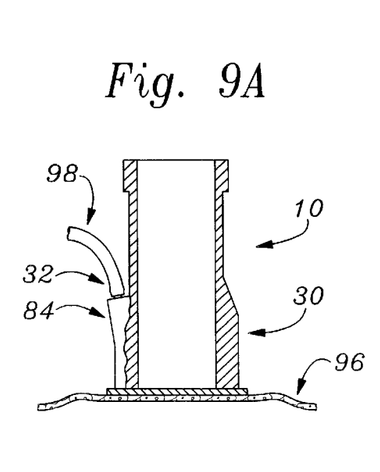
FIG. 9a is a side view of the tissue stabilizer of the present invention attached to tissue.
Figure 9B:
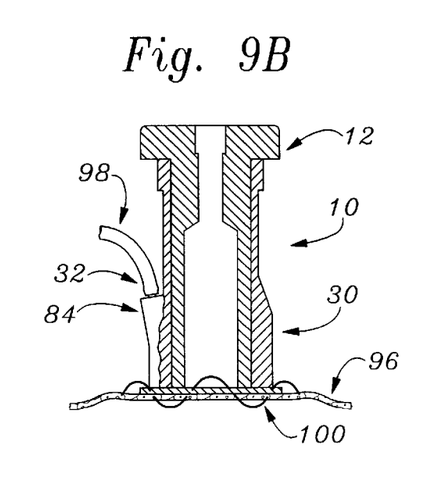
FIG. 9b is a side view of the tissue stabilizer of the present invention attached to tissue and having a needle guide positioned therein.

To utilize the present invention the operator gains access to the viscus body or hollow organ. For example, in procedures involving the heart, one approach to the heart requires the patient be positioned for a left anterolateral thoracotomy. An incision is made in the patient's chest and the chest is entered through the bed of the respected fifth rib. The pericardium is incised posterior and parallel to the left phrenic nerve, such that the incision extends from the left pulmonary artery to the apex of the left ventricle. As shown in FIG. 9a, the tissue stabilizer 10 having a vacuum conduit in communication with the vacuum port 32 located thereon is positioned proximate the area of interest such that the attachment flange 30 of the tissue stabilizer 10 engages the tissue portion 96. As shown in FIG. 9b, the needle guide 12 is positioned on and sealably engages the tissue stabilizer 10. Thereafter, an external vacuum source (not shown) in communication with the vacuum conduit 98 is activated. The vacuum force is applied through the vacuum chamber 34 to the tissue portion 96, resulting in the tissue stabilizer 10 attaching to the tissue portion 96. In an alternate embodiment, a second independent vacuum source is in communication with the central lumen 26, thereby increasing the vacuum force applied to the tissue portion 96. As shown in FIG. 9b, a purse string suture 100 may then be applied to the tissue portion 96 through the suture template 38.

Figure 9C:
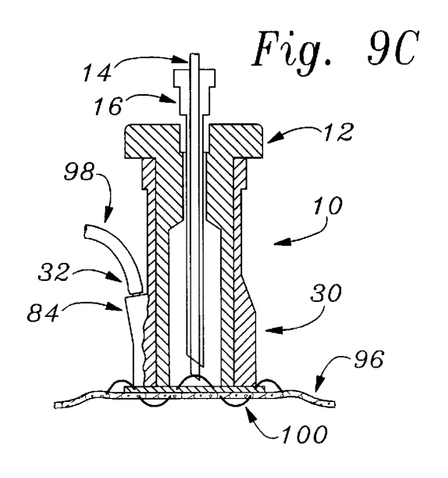
FIG. 9c is a side view of the tissue stabilizer of the present invention attached to tissue and having a needle guide positioned containing an obturator and a puncture device positioned therein.
Figures 9D, 9E:
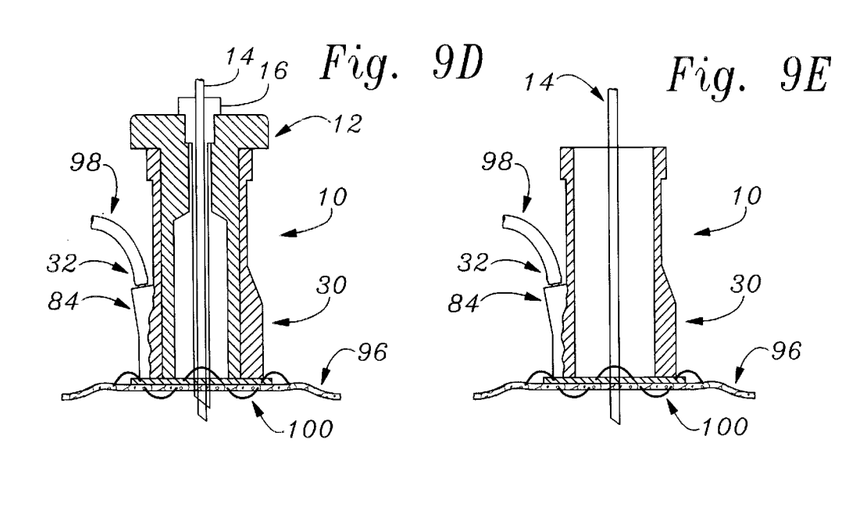
FIG. 9d is a side view of the tissue stabilizer of the present invention attached to tissue and having a needle guide positioned containing an obturator and a puncture device puncturing the tissue.
FIG. 9e is a side view of the tissue stabilizer of the present invention attached to tissue and having a puncture device positioned therein.

FIG. 9c shows an obturator 16 containing a puncture device 14 inserted through the receiving aperture 46 of the needle guide 12 and positioned within the central lumen 26 of the tissue stabilizer 10. The distal portions of the puncture device 14 and obturator 16 are advanced to a position proximate the tissue portion 96. Referencing FIG. 9d, the distal portion of the puncture device 14 is manually advanced through the central lumen 28 and punctures the tissue portion 96, thereby entering the viscus region 102. Thereafter, the distal portion of the obturator 16 is advanced into the viscus region, thereby enlarging the puncture hole. The needle guide 12 and obturator 16 may then be removed. FIG. 9e shows the puncture device 14 positioned within the tissue stabilizer 10.

Figure 9F:
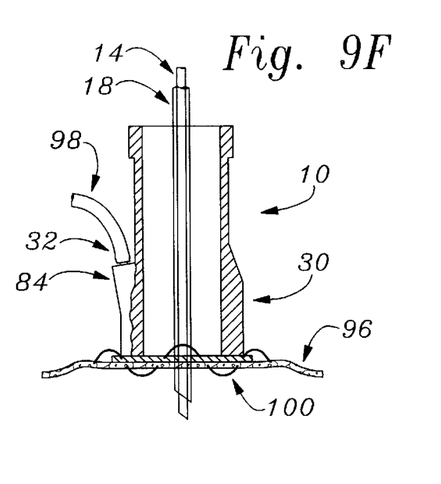
FIG. 9f is a side view of the tissue stabilizer of the present invention attached to tissue and having a removable dilator and a puncture device positioned therein.

Referencing FIG. 9f, a removable dilator 18 is positioned over the puncture device and advanced through the central lumen 26 of the tissue stabilizer 10, entering the viscus region through the puncture hole. Thereafter the puncture device 14 is removed from the tissue stabilizer 10.

Figure 9G:
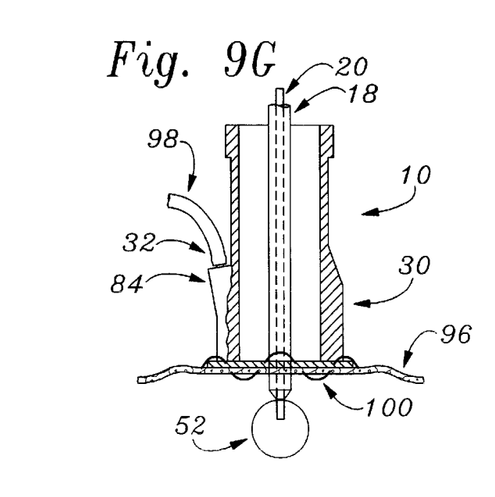
FIG. 9g is a side view of the tissue stabilizer of the present invention attached to tissue and having a removable dilator and a sealing device positioned therein.
Figure 9H:
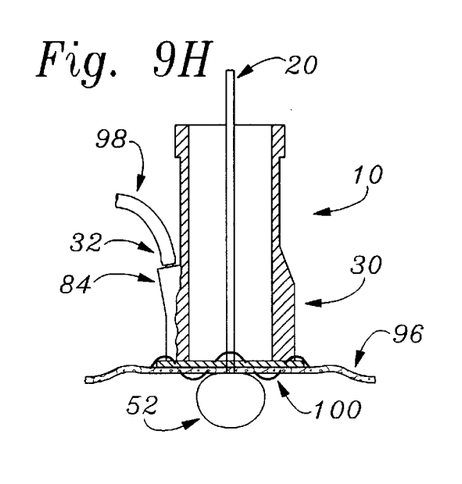
FIG. 9h is a side view of the tissue stabilizer of the present invention attached to tissue and having a sealing device positioned thereon.

As shown in 9g, the deployable sealing device 20 is inserted into the removable dilator 18 and the sealing balloon 52 of the sealing device 20 is advanced through the removable dilator 18 entering the viscus region. As FIG. 9g shows, the inflation device 50 is actuated causing the sealing balloon 52 to inflate and sealably engage the tissue portion 96 within the viscus region. As shown in FIG. 9h, the removable dilator 18 may then be removed leaving the sealing device positioned within the tissue stabilizer 10.

Figure 9I:
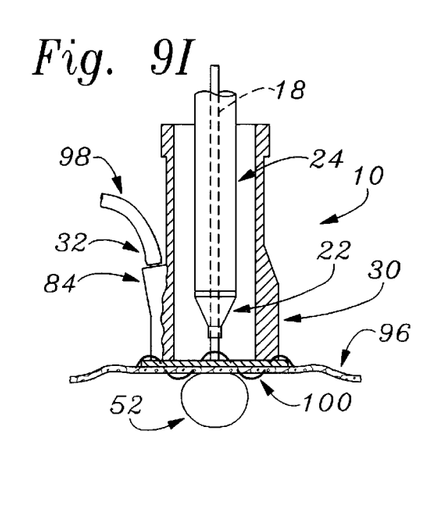
FIG. 9i is a side view of the tissue stabilizer of the present invention attached to tissue and having a sealing cannula containing a cutting trocar positioned thereon.
Figure 9J:
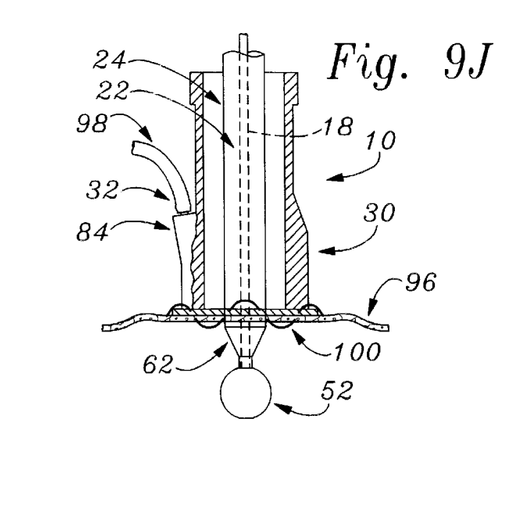
FIG. 9j is a side view of the sealing cannula of the present invention having a cutting trocar and sealing device positioned thereon.
Figure 9K:
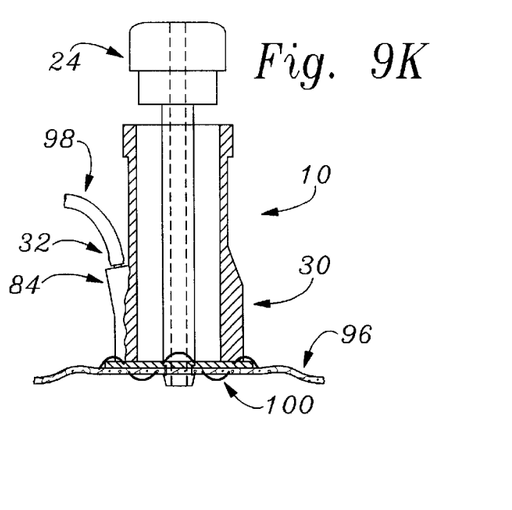
FIG. 9k is a side view of the sealable cannula of the present invention attached to tissue.

As shown in FIG. 9i, the cutting trocar 22 has been inserted through the sealing cannula 24 such that the trocar insertion outlet 60 emerges from the device outlet 95 formed in the sealing cannula 24. As shown in FIG. 9i, the sealing cannula 24 containing the cutting trocar 22 is advanced along the transfer lumen 48 of the sealing device 20, and is progressed through the central lumen 26 of the tissue stabilizer 10. FIG. 9j shows the blunt end 60 of the trocar engaging and displacing the balloon 52. The cutting head 62, which is disposed on the distal portion of the cutting trocar 22, engages and advances through the tissue portion 96, resulting in the tissue portion 96 engaging the tissue engaging channel 72 formed on the distal portion of the sealing cannula 24. As shown in FIG. 9j, the vacuum force applied to the tissue stabilizer 10 is terminated and the purse string suture 100 is tightened about the tissue engaging channel 72 of the sealing cannula 24. As shown in FIG. 9k, the cutting trocar 22 and sealing device 20 are removed from the sealing cannula 24.

Figure 10A:
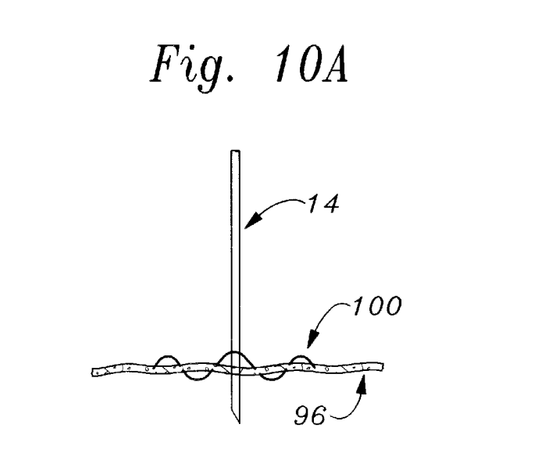
FIG. 10a shows an alternate method of accessing a viscus region or hollow organ wherein a puncture device is inserted into tissue.
Figure 10B:
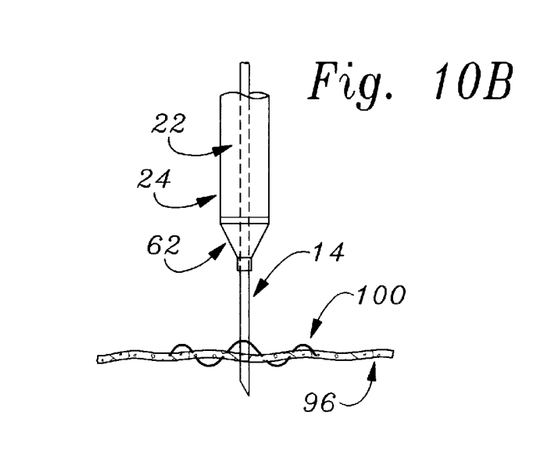
FIG. 10b shows an alternate method of accessing a viscus region or hollow organ wherein a cutting trocar positioned within a sealing cannula is advanced on a puncture device is inserted into tissue.
Figure 10C:
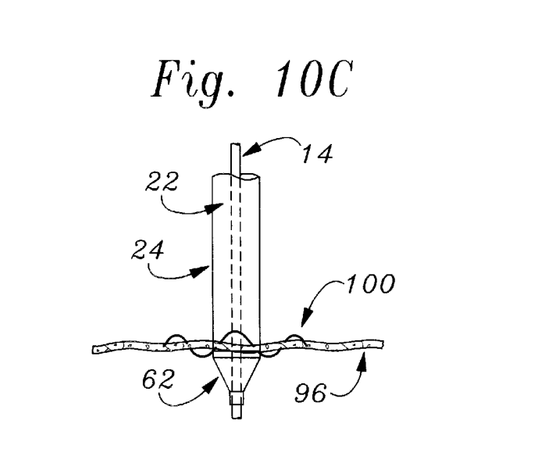
FIG. 10c shows an alternate method of accessing a viscus region or hollow organ wherein the cutting trocar positioned within a sealing cannula is engaging tissue.
Figure 10D:
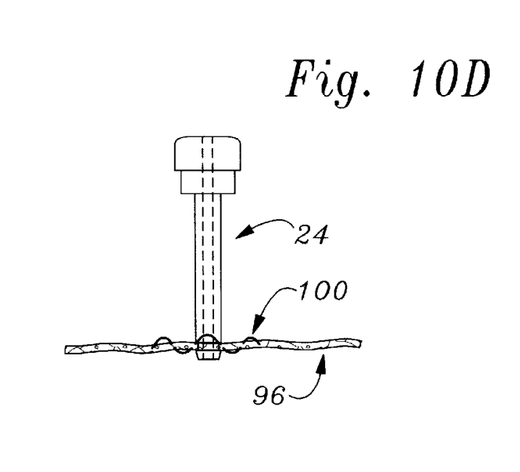
FIG. 10d shows an alternate method of accessing a viscus region or hollow organ wherein the sealing cannula is sealably positioned on tissue.

An alternate method of accessing a viscus region or hollow organ is illustrated in FIGS. 10a–10d. In this alternate embodiment, the reference numerals 14, 22, 24, 62, 72, 95, 96, and 100 have analogous meanings to the reference numerals identifying the features of the previous embodiment. As with the previous embodiment, access to the area of interest is gained in accordance with methods generally known in the art. As shown in FIG. 10a, a puncture closing mechanism, for example a purse string suture 100, is applied to the tissue 96. The distal portion of the puncture device 14 is advanced through the tissue 96, thereby forming a puncture hole. The cutting trocar 22 is inserted through the sealing cannula 24 such that the trocar insertion outlet 62 emerges from the device outlet 95 formed in the sealing cannula 24. As shown in FIG. 10b, the sealing cannula 24 containing the cutting trocar 22 is advanced along the puncture device 14. As shown in FIG. 10c, the cutting head 62, which is disposed on the distal portion of the cutting trocar 22, engages and advances through the tissue portion 96, resulting in the tissue portion 96 engaging the tissue engaging channel 72 formed on the distal portion of the sealing cannula 24. FIG. 10d shows the purse string suture tightened around the tissue enagging channel 72, after the cutting trocar 22 and puncture device 14 have been withdrawn.

In closing it is understood that the embodiments of the invention disclosed herein are illustrative of the principles of the invention. Other modifications may be employed which are within the scope of the invention; thus, by way of example but not of limitation, alternative sealing devices, alternative cutting devices, and alternative sealing members included within the sealing cannula 24. Accordingly, the present invention is not limited to that precisely as shown and described in the present invention.

What is claimed is:

1. A system for providing sealed access to a viscus or hollow body, comprising:

a tissue stabilizer having a lumen formed therein, said tissue stabilizer attachable to a viscus or hollow body;

a needle guide attachable to said tissue stabilizer, said needle guide having a receiving aperture formed therein;

a puncture device capable of forming a puncture hole in tissue;

an obturator engagable with said needle guide, said obturator having a obturator lumen capable of receiving said puncture device;

a removable dilator comprising a dilator lumen capable of receiving said puncture device;

a sealing device deliverable to said puncture hole through said removable dilator;

a cutting trocar comprising a distal portion having at least one tissue cutting member and a sealing device port, said trocar further comprising a trocar lumen formed therein, and a sealing cannula comprising a sealable cannula lumen capable of sealably receiving said cutting trocar.

2. The system of claim 1 wherein said tissue stabilizer further comprises a vacuum port, said vacuum port communicable with a vacuum source.

3. The system of claim 2 wherein said tissue stabilizer further comprises a vacuum chamber in communication with said vacuum port.

4. The system of claim 3 wherein tissue stabilizer further comprises vanes disposed within said vacuum chamber.

5. The system of claim 1 wherein said tissue stabilizer further comprises a suture template.

6. The system of claim 1 wherein said needle guide is sealably engageable with said tissue stabilizer.

7. The system of claim 1 wherein said puncture device is a needle.

8. The system of claim 1 wherein said puncture device is a guide wire.

9. The system of claim 1 wherein said obturator is sealably engageable with said needle guide.

10. The system of claim 1 wherein said removable dilator is a peel-away dilator.

11. The system of claim 1 wherein said removable dilator is sealably engageable with said tissue stabilizer.

12. The system of claim 1 wherein said sealing device is a inflatable balloon, said balloon in communication with an inflation device through an inflation lumen.

13. The system of claim 12 wherein said sealing device is inflated with a biologically inert fluid.

14. The system of claim 12 wherein said inflation device is a syringe.

15. The system of claim 1 wherein said cutting trocar comprises three tissue cutting members.

16. The system of claim 1 wherein said cutting trocar comprises four tissue cutting members.

17. The system of claim 1 wherein said trocar lumen is in communication with said sealing device port and a trocar receiving orifice.

18. The system of claim 1 wherein the distal portion of said sealing cannula comprises tissue engaging channel.

19. The system of claim 1 wherein said cannula lumen comprises a sealing member.

20. The system of claim 19 Wherein said sealing member comprises a duckbill seal.

21. The system of claim 19 wherein said sealing member comprises a flapper seal.

* * * * *